United States Patent [19]

Schütz

[11] Patent Number: 4,465,461
[45] Date of Patent: Aug. 14, 1984

[54] DENTAL-ORTHODONTIC DEVICE

[76] Inventor: Winfried Schütz, Ravensburger Ring 63, 8000 München 60, Fed. Rep. of Germany

[21] Appl. No.: 407,427

[22] Filed: Aug. 12, 1982

[30] Foreign Application Priority Data

Aug. 14, 1981 [DE] Fed. Rep. of Germany ....... 3132242
Jan. 28, 1982 [DE] Fed. Rep. of Germany ....... 3202708

[51] Int. Cl.³ .............................................. A61C 7/00
[52] U.S. Cl. ........................................................ 433/3
[58] Field of Search ............................................ 433/3

[56] References Cited

U.S. PATENT DOCUMENTS 4,035,919 7/1977 Cuszto .................................... 433/3
4,167,063 9/1979 Sosnay .................................... 433/3

Primary Examiner—Robert Peshock
Attorney, Agent, or Firm—Hayes, Davis & soloway

[57] ABSTRACT

The invention relates to a dental-orthodontic device or instrument comprising an essentially straight handle and a working head which is particularly suited for the precise placement of adhesive brackets on tooth surfaces. Between its handle and its working head the instrument is approximately U-shaped, consequently, when the device is used, the handle is outside the oral cavity of the patient. When positioning the brackets on the teeth, the corners of the mouth and the cheeks of the patient, stabilized by a "lip-retractor", lie in the U-shaped portion of the instrument. In addition, the working head is disposed in the extension of the central axis of the handle. The instrument may also be constructed in such a way that is resembles a pair of tweezers.

11 Claims, 12 Drawing Figures

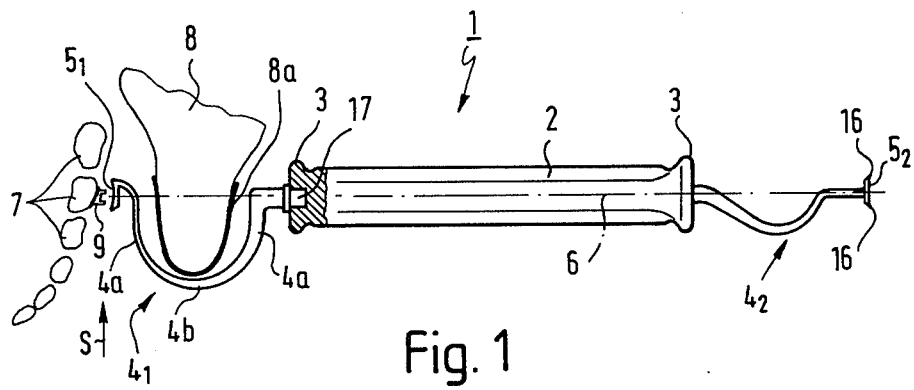
Fig. 1
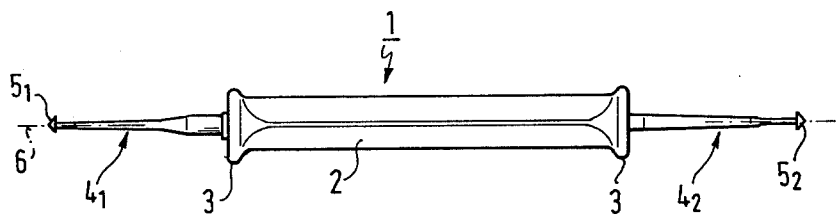
Fig. 2
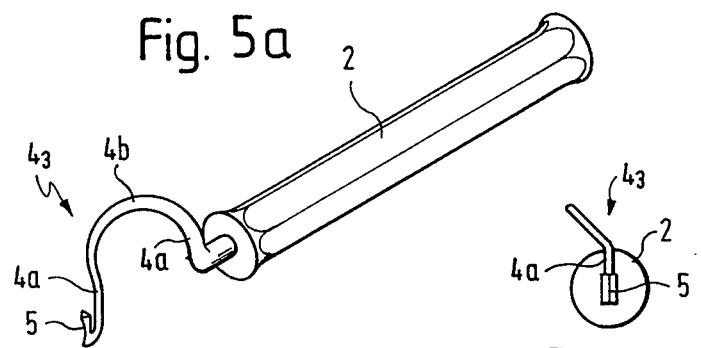
Fig. 5a
Fig. 5b

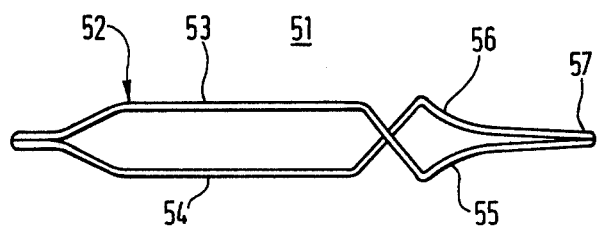
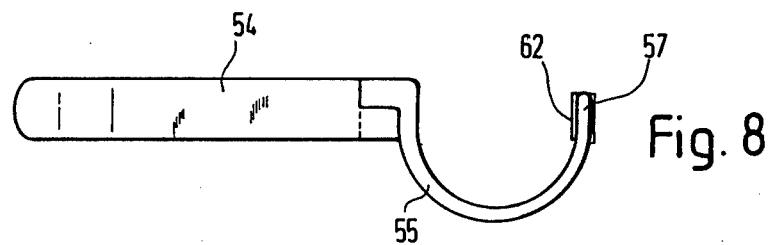
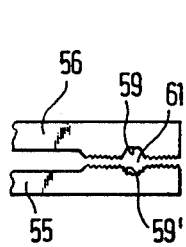
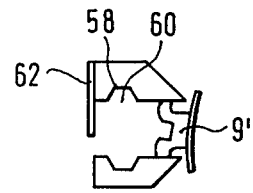
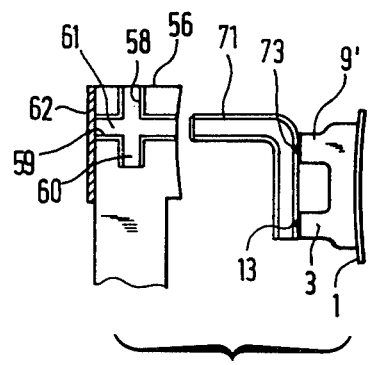

DENTAL-ORTHODONTIC DEVICE

TECHNICAL FIELD OF THE INVENTION

The present invention relates to a dental-orthodontic device or instrument for use by dentists, particularly to a device which is especially adapted to position adhesive brackets, i.e. a bracket alignment device or bracket aligner.

BRIEF DESCRIPTION OF THE PRIOR ART

In dentistry, use is made, for example, for orthodontic purposes, of so-called adhesive brackets which are adhered to the surfaces of all teeth by means of a base plate and which are subsequently connected by means of a regulating wire which is threaded through slots which are on the brackets. In doing this, it is necessary to position the brackets on the tooth surface with high accuracy, taking care that the bracket slot is placed accurately with predetermined angular tip in relation to the tooth axis. In positioning the bracket, it is, therefore, necessary to press the bracket base against the tooth surface and to place the bracket slot in its proper working position (angular tip). The device with which the bracket is placed on the tooth should be constructed so that a perpendicular force may be exerted on the surface of the teeth in the final positioning of the brackets; in addition, the device should be adapted to be easily rotated in order to move the bracket slot into the correct angular position. Finally, it should be possible to change the position of the bracket before it is definitely fixed in position.

Where such operations have to be performed, it is important that an instrument be available which, while affording an unobstructed view of the working area, is adapted to be employed in an accurately controlled manner. Various instruments such as scalers and similar instruments are in use.

As regards the front sections of the maxilla and mandible (cuspid area to cuspid area), hardly any problems will arise because these sections are easily accessible when the patient's mouth is open. Different working conditions, however, arise in the premolar areas where the working area is not easily accessible and where the view is obstructed. This is partly due to the fact that the dentist has to hold the instrument at a relatively acute angle in relation to the tooth surface and that his view is obstructed by both the instrument and his fingers.

Therefore, the conventional hand instruments are not suited to handle such brackets placement in a satisfactory manner.

OBJECT OF THE INVENTION

It is an object of the present invention to provide a dentist's instrument of the aforeindicated type which is adapted to be handled in a controlled manner, by means of which forces can be accurately transmitted within a given working area and which is particularly adapted to grip adhesive brackets in a reliable manner.

SUMMARY OF THE INVENTION

According to the invention, said objects are attained by the provision of an instrument which is provided between its handle and its working head with a U-shaped section, with the working head being disposed on an extension of the handle longitudinal axis. With said instrument being constructed in this manner, said U-shaped portion or working head supporting yoke, when in its position of use, extends away from the working area and around the corners of the patient's mouth. This serves to give an unobstructed view of the working area. Moreover, the working head is disposed on an extension of the central axis of the handle which is completely outside the oral cavity. Thus it is possible for the dentist to apply the desired forces accurately in the direction of the handle, that is to say, to apply forces perpendicularly to the tooth surface, this is not possible with conventional instruments. Moreover, due to this arrangement it is easily possible to rotate the working head about the axis of the handle so that the instrument may be moved in an accurately controlled manner.

BRIEF DESCRIPTION OF THE DRAWINGS

The invention and further particulars will be described more specifically hereinafter with reference to preferred embodiments shown in the drawings, in which:

FIG. 1 is a side elevation of an instrument according to the invention adapted to position adhesive brackets;

FIG. 2 is a plan view of the instrument of FIG. 1;

FIGS. 5a and 5b respectively show in a perspective view and a plan view a second embodiment of the invention;

FIG. 7 is a plan view of another embodiment of an instrument according to the invention constituting a pair of tweezers;

FIG. 8 is a side elevation of the instrument illustrated in FIG. 7;

FIG. 9 is a fragmentary plan view showing the pointed ends of the two arms of the tweezer-type instrument shown in FIGS. 7 and 8;

FIG. 10 is a front elevational view of the pointed ends of the two tweezer arms of the instrument and FIG. 11 is a fragmentary side elevation of a tweezer arm illustrating its use in positioning a bracket.

DETAILED DESCRIPTION OF THE PREFERRED EMBODIMENTS OF THE INVENTION

Figure 3:
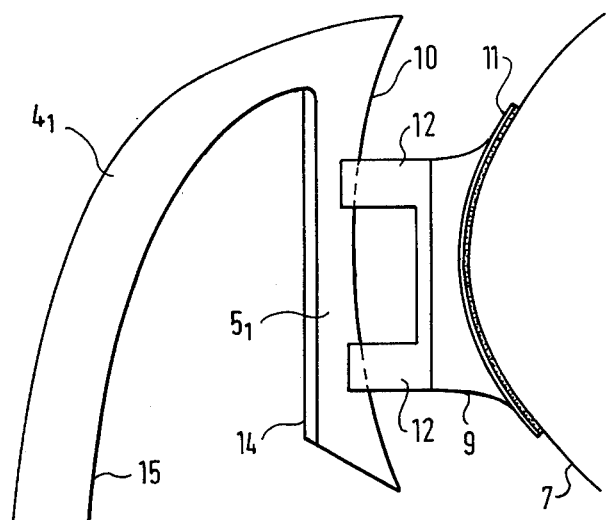
FIG. 3 is a fragmentary plan view of the working head portion of the instrument of FIGS. 1 and 2 and illustrates the positioning of an adhesive bracket.

A hand instrument 1 as shown in the drawing comprises a straight handle 2 having a hexagonal cross section provided on either end with a supporting bead 3, a supporting yoke $4_1$ extending from one end of said handle and a working head $5_1$ disposed on the free end of the U-shaped supporting yoke. The opposite end of handle 2 is provided with another U-shaped supporting yoke $4_2$ having a working head $5_2$. Each of said two supporting yokes comprise two legs 4a and a connecting portion 4b between the respective legs.

FIGS. 1 and 2 are drawn on a scale of approximately 1:1.2. The handle has a length of approximately 8 cm, and the supporting yokes $4_1$ and $4_2$ carrying the working heads $5_1$ and $5_2$, respectively extend approximately 3.5 cm beyond the ends of the handle. The two working heads are disposed on extensions of the longitudinal axis 6 of the straight handle. The U-shaped supporting yoke $4_1$ has an unobstructed depth of between 1.5 and 2 cm as measured from axis 6, whereas the free depth of the U-shaped supporting yoke $4_2$ amounts to between 0.5 and 0.8 cm. The part of the instrument comprising the supporting yoke $4_1$ having the greater depth permits the instrument to be introduced deeply into the oral cavity so as to permit, for example, manipulations to be performed on the premolars, this being diagrammatically shown in FIG. 1 where several teeth are shown at 7. In this case the instrument is inserted into the oral cavity in such a manner that the corners of the mouth diagrammatically shown at 8 can be reached by the U-shaped supporting yoke. To prepare such a manipulation, it is convenient first to introduce a so-called lip retractor for the purpose of holding the lips and cheeks of the patient away from the teeth and to stabilize their shape. In this position, the working head of the instrument is disposed directly opposite a tooth 7 which is to be provided with an adhesive bracket 9, handle 2 being arranged outside the oral cavity. As seen in FIG. 1, the dentist performing the manipulation has an unobstructed view of the working area in the direction of arrow S. The instrument including the working head disposed on an extension of central axis 6 may be pushed against the tooth or rotated or pivoted as desired without the view of the working area being obstructed.

While working head $5_1$ carried by the deep supporting yoke $4_1$ permits manipulations to be conveniently carried out on the praemolars, the second working head $5_2$ mounted on the U-shaped supporting yoke $4_2$ having a smaller depth is employed for work to be performed on the cuspids and incisors which require the working head to be introduced into the oral cavity to a smaller depth only.

Figure 4:
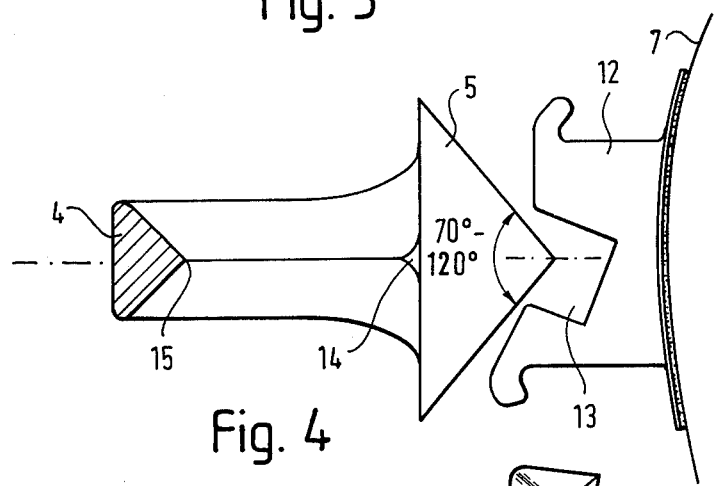
FIG. 4 illustrates the use of the working head of the instrument in positioning an adhesive bracket.

The shape of the working heads $5_1$ and $5_2$ for positioning adhesive brackets is shown in FIGS. 3 and 4. The working head 5 is constructed as a generally straight bar member having a triangular cross section the apex angle of which ranges between 70° and 90° the front edge 10 of the bar member being of slightly concave shape as seen in FIG. 3. This shape affords the advantage explained below. The adhesive bracket 9 is provided with a base plate 11 which is adapted to be adhesively secured to a tooth 7. Extending from base plate 11 are two lateral arms 12 each of which is provided with a bracket slot 13. Each said bracket slot having a generally rectangular cross-section is provided with a predetermined torque in relation to the tooth axis, this torque depending on the nature of the tooth the position of which is to be regulated. With working head 5 of wedge shape, it is possible to insert its front edge 10 into the bracket slot, there being no risk of the working head being jammed in bracket slot 13; thus it will always be possible easily to withdraw the instrument from the bracket slot. The length of working head $5_1$ is greater than the distance between the external edges of the arms 12 of adhesive bracket 9.

With the front edge 10 of the wedge-shaped working head 5 being introduced into bracket slot 13, the concave shape of front edge 10 facilitates centering the adhesive bracket. In its actual position of use. the working head will extend by approximately equal amounts beyond the two arms 12 of bracket 9 as shown in FIG. 3. This ensures reliable support and positioning for the adhesive bracket.

During positioning of the adhesive bracket it is also necessary to adjust the tip of bracket slot 13 in relation to the axis of the tooth crown. Besides the torque position already mentioned, this angulation is of importance in relation to the correct final position of the respective tooth to be obtained. With the working head in its position of use as shown in FIGS. 3 and 4, the desired tip position can be easily obtained by rotating handle 2 since such rotary motion is directly transmitted to the working head. In order to facilitate the attainment of this angular position, the rear edge of the working head may additionally be provided with a sighting edge 14. The U-shaped supporting yoke 4 may also be provided with a sighting edge 15. In the simplest case, the U-shaped supporting yoke 4 also has a triangular cross section as shown in FIG. 4. The apex of this portion facing the working head then constitutes said sighting edge 15. As the bracket is being positioned, it is possible by sighting along said edges 14 and 15 easily to obtain the desired angular position of bracket slot 13.

Instead of providing working head 5 with a concave front edge 10, it is also possible to provide a straight edge as shown in FIG. 1 for working head $5_2$. For the purpose of centering and fixing the bracket, both ends of this working head may be provided with small pointed teeth 16. In this case, working head $5_2$ is of T shape, one portion of the T shape being disposed on an extension of central axis 6 of handle 2. The U-shaped supporting yoke $4_2$ is then attached to the proximate end of this portion.

With particularly strongly inclined teeth, particularly premolars, it may happen in rare cases that the connecting bight 4b of U-shaped supporting yoke 4 between the two legs 4a interferes with the corner of the mouth or the lips of the patient. For such extreme cases the U-shaped supporting yoke $4_3$ shown in FIG. 5 is employed; in this case the bight portion 4b between the two legs is angulated in such a way that the plane of the bight portion forms an angle of approximately 45° with said legs. In using this instrument, the angulated portion may be disposed to extend about the corners of the mouth or the lips of the patient, respectively, even in the case of extreme rotary positions without manipulations being impeded.

Figure 6:
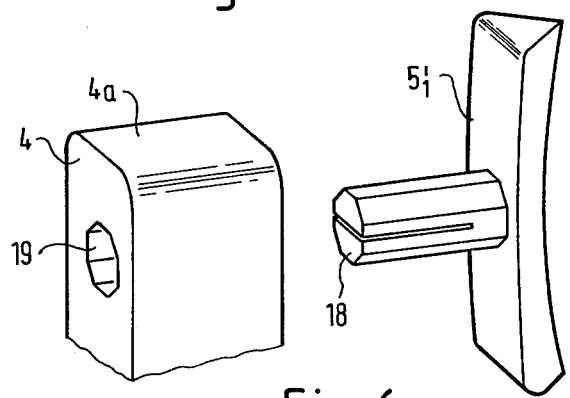
FIG. 6 is a fragmentary perspective view of the working head of another embodiment of an instrument according to the invention.

In addition, it is possible with the instrument according to the invention to provide a plug-in connection between the U-shaped supporting yoke and the handle. In such a case it is only necessary to provide a single handle and a plurality of plug-in supporting yokes. In FIG. 1, such a plug-in connection 17 is represented diagrammatically. Moreover, it is possible to employ such a plug-in connection between a working head $5_1'$ and the U-shaped supporting yoke in order to provide a detachable connection for the working head as shown in the fragmentary perspective representation in FIG. 6. The working head $5_1'$ is approximately of T-shape, the transverse portion of the head being provided with a coupling portion 18 having an octagonal cross section and a longitudinal slot; coupling portion 18 is adapted to be received by an octagonal aperture 19 provided on the free end of the respective U-shaped leg 4a of the supporting yoke 4, it being possible to lock portion 18 in aperture 19. The octagonal cross section of portion 18 and aperture 19 permits the angular position of the working head to be selected in steps of 45° each.

Shown in FIGS. 7 to 11 is another embodiment of an instrument according to the invention which is adapted to grasp an adhesive bracket. The instrument 51 resembles a pair of holding tweezers and comprises a handle 52 including two limbs 53, 54 made of spring steel. Connected to handle 52 are two U-shaped tweezer arms 55, 56, said limbs crossing each other between the tweezer arms. Forcing limbs 53 54 of handle 52 together will cause the holding tweezers to open. The U-shaped or arched tweezer arms 55, 56 may be easily introduced into the oral cavity of the patient, it being possible for the corners of the patient's mouth to be received by the U-shaped portions. The pointed free ends of the tweezer arms form a wedge-shaped working head 57 which is disposed on an extension of handle 52. With the aid of working head 57 it is possible to grasp brackets 9' by the bracket wings and to manipulate such brackets. However, it is also possible to insert working head 57 into a bracket slot as described earlier. The working head corresponds to the head shown in FIG. 4, it being assumed that the head of FIG. 4 is separated into two parts along its axis of symmetry. Thus the dentist is in a position to transmit from the handle to the working head both thrust and rotary forces in a suitable manner.

As shown in FIGS. 8 to 10, it is additionally possible, in the area of working head 57, to provide the two tweezer arms 55 and 56 with two intersecting trough-shaped recesses 58 and 59 which in the present case, are of approximately trapezoidal cross section so that, with the tweezer arms closed, apertures 60 and 61 having straight axes and a hexagonal cross section are formed, said apertures intersecting each other at right angles. Tweezers 51 permit manipulation of brackets 9' which are provided with a holding pin 71 adapted to be broken off.

Holding pin 71 in the present case has a hexagonal cross section as have the apertures 60 and 61 formed upon the tweezers being closed; pins 71 are attached to bracket 9', for example, by spot welding. Other cross-sectional shapes of the holding pin and the apertures may also be selected, the only condition to be met being that it should be possible immovably to hold the bracket in position.

Depending on the part of the jaw to which manipulations are to be directed, for example where an adhesive bracket is to be mounted on the surface of a tooth, the holding pin 11 of the bracket is inserted either into aperture 60 or aperture 61 of instrument 51. Where operations have to be performed, for example, on the rear teeth of the upper or lower jaw, the holding pin of the adhesive bracket is inserted into the aperture 61 of the instrument which approximately extends along the axis of the instrument. Where the front part of a jaw is involved, aperture 60 extending at right angles to aperture 61 is employed for retaining the adhesive bracket. It is a particular advantage of the instrument according to the invention that after accurately positioning the bracket the instrument can be easily detached from the holding pin without the bracket being displaced.

It should be understood that it is not necessary to cause the cross section of the trough-shaped slots or depressions 58, 59 to match the cross section of holding pins 11. It is only necessary for such recesses or slots to have surfaces such that the holding pins of brackets may be held in such a way that undesired rotation is prevented. For example, there is shown in FIG. 8 a serrated recess 59'.

With this arrangement it is possible also to manipulate adhesive brackets in the area of the lateral teeth, particularly where the teeth are heavily rotated out of their normal positions.

In addition, one of the tweezer arms, such as tweezer arm 56, may be provided in the area of working head 57 with an abutment plate 62 which is adapted, with the tweezer arm closed, to close the aperture 61 which extends in the direction of the longitudinal axis of the instrument. This arrangement ensures that holding pin 71 of a bracket can only be introduced to a depth defined by the abutment plate. Thus, dependable support of the bracket during its manipulation is ensured.

What is claimed is:

1. A dental-orthodontic device to position and angularly align a slotted adhesive bracket, which has been placed on a tooth surface in an oral cavity of a patient, before the adhesive has set, comprising a substantially straight handle and a working head shaped to engage the slot of said bracket to position and angularly align said bracket on said tooth surface, said instrument being U-shaped between said handle and said working head to form a U-shaped supporting yoke wherein, during the use of the instrument, the corners of the mouth and the cheek of the patient may be received by the U-shaped supporting yoke with the handle being disposed outside of the oral cavity and perpendicular to the tooth surface, said working head being disposed on an extension of the central axis of said handle, said working head being constructed as an elongate wedge member of triangular cross section and extending approximately at right angles to the central axis of said handle, the length of the wedge member being sufficient to allow the desired angular alignment and positioning of said bracket.

2. The device of claim 1, characterized in that said U-shaped supporting yoke, in the connecting area between the two legs of said yoke, is angulated preferably by approximately 45° out of the plane containing said legs.

3. The device of claim 1, characterized in that said U-shaped supporting yoke is adapted to be connected to said handle by means of a plug-in arrangement.

4. The device of claim 1, characterized in that the front edge of said working head is of concave shape.

5. The device of claim 1, characterized in that the front edge of said working head is straight and that one pointed portion is formed on each end of said front edge.

6. The device of claim 1, characterized in that the rear surface of said working head facing said handle is provided with a sighting edge.

7. The device of claim 6, characterized in that a sighting edge is formed on said U-shaped supporting yoke at least in the area facing said working head.

8. The device of claim 6, characterized in that said U-shaped supporting yoke has a triangular cross section with the apex of the cross section facing said working head where it extends in the vicinity of said working head.

9. The device of claim 1, characterized in that said instrument is constructed as a pair of tweezers.

10. The device of claim 9, characterized in that said pair of tweezers is constructed as a pair of gripping tweezers.

11. The device of claim 10, characterized in that, with the tweezer arms closed, said working head defines two mutually perpendicular apertures, one of said apertures approximately extending along an extension of the longitudinal axis of said handle, the other aperture extending approximately perpendicularly thereto towards the ends of said tweezer arms.

* * * * *